(12) United States Patent
Feingold et al.

(10) Patent No.: US 6,406,481 B2
(45) Date of Patent: *Jun. 18, 2002

(54) METHOD PRELOADING A DEFORMABLE INTRAOCULAR LENS INTO INJECTING APPARATUS FOR STORAGE AND/OR SHIPMENT

(75) Inventors: Vladimir Feingold, Laguna Niguel; Daniel C. Eagles, Capistrano Beach, both of CA (US)

(73) Assignee: Starr Surgical Company, Inc., Monrovia, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/038,053

(22) Filed: Mar. 11, 1998

Related U.S. Application Data

(60) Division of application No. 08/747,308, filed on Nov. 12, 1996, now Pat. No. 5,728,102, which is a continuation of application No. 08/345,360, filed on Nov. 18, 1994, now abandoned, and a continuation-in-part of application No. 08/225,060, filed on May 10, 1994, and a continuation-in-part of application No. 08/220,999, filed on Apr. 1, 1994, now abandoned, and a continuation-in-part of application No. 08/197,604, filed on Feb. 17, 1994, now Pat. No. 5,499,987, and a continuation-in-part of application No. 08/196,855, filed on Feb. 15, 1994, now Pat. No. 5,436,770, and a continuation-in-part of application No. 08/195,717, filed on Feb. 14, 1994, now abandoned, and a continuation-in-part of application No. 07/953,251, filed on Sep. 30, 1992, now abandoned.

(51) Int. Cl.$^7$ .................................................. A61F 9/00
(52) U.S. Cl. ...................................................... 606/107
(58) Field of Search ................................. 606/107, 166; 623/6

(56) References Cited

U.S. PATENT DOCUMENTS

| 4,681,102 A | * | 7/1987 | Bartell ........................ 606/107 |
| 4,919,130 A | * | 4/1990 | Stoy et al. .................. 606/107 |
| 5,123,905 A | * | 6/1992 | Kelman ....................... 606/107 |
| 5,921,989 A | * | 7/1999 | Deacon et al. .............. 606/107 |
| 5,928,245 A | * | 7/1999 | Wolf et al. .................. 606/107 |

* cited by examiner

Primary Examiner—Kevin T. Truong
(74) Attorney, Agent, or Firm—William L. Klima; Law Offices of William L. Klima, P.C.

(57) ABSTRACT

An intraocular lens injection system comprising an injecting device and cartridge. The cartridge comprises a lens holding portion and an outer sleeve portion. The invention includes a method of pre-loading the injecting system, particularly the cartridge, to reduce the amount of packaging, prevent damage to the intraocular lens during packaging and shipping, allow the pre-loaded injecting cartridge to be autoclaved as a unit, and eliminate the step of loading the cartridge with the intraocular lens by the end user to prevent potential damage during this step.

15 Claims, 9 Drawing Sheets

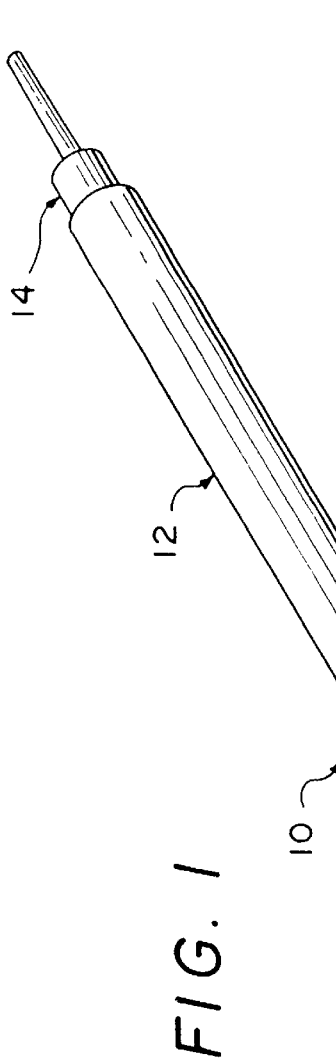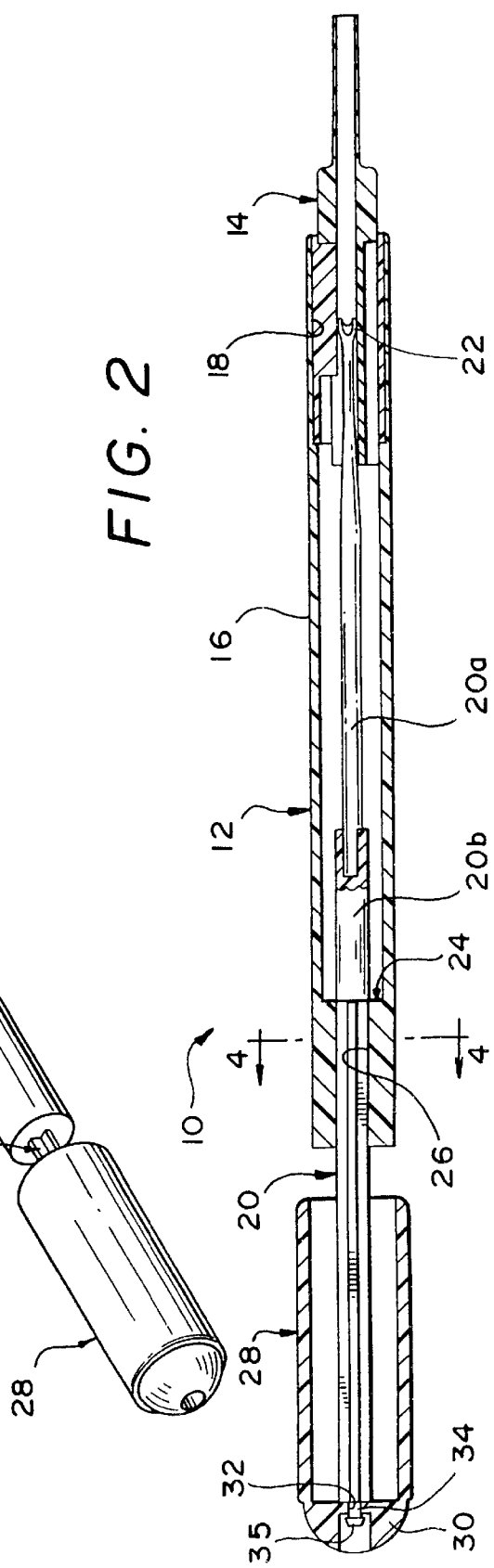

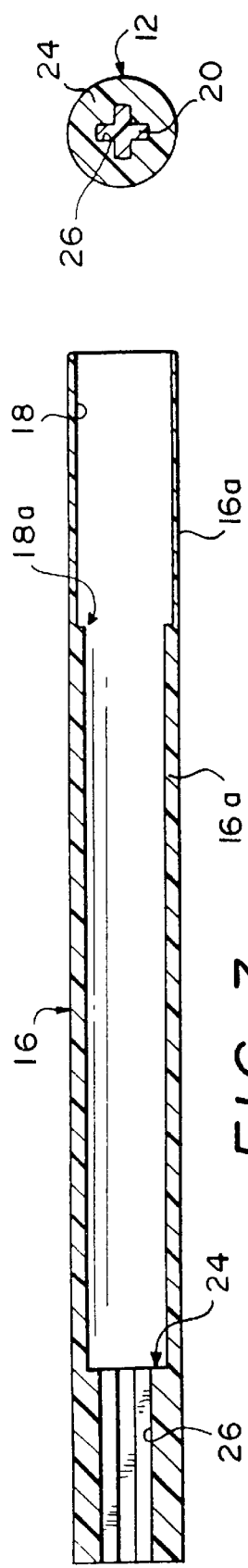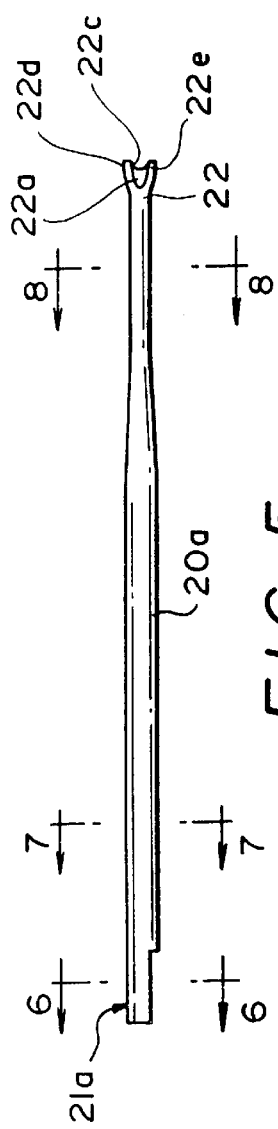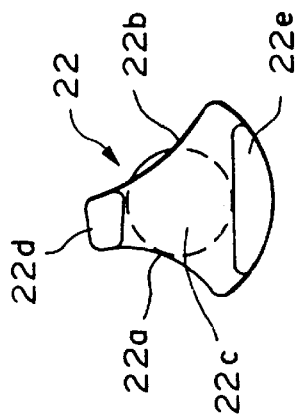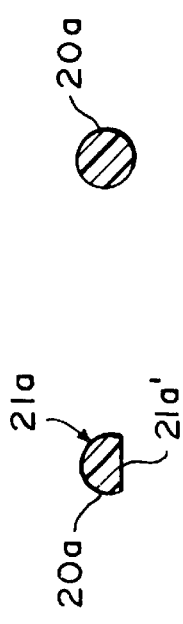

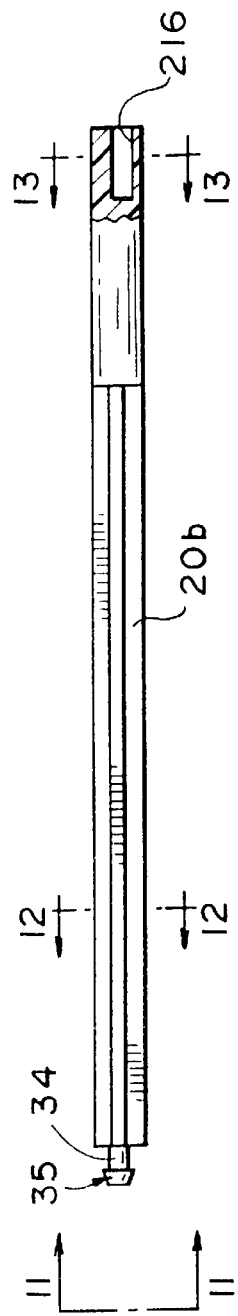
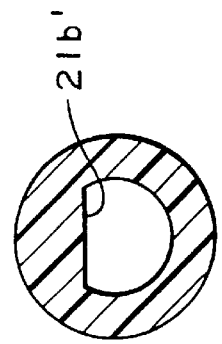
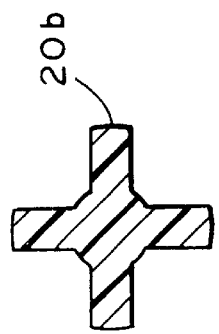
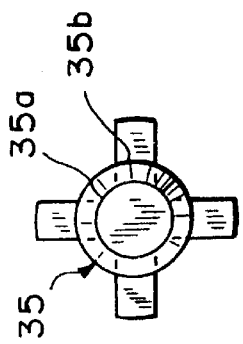
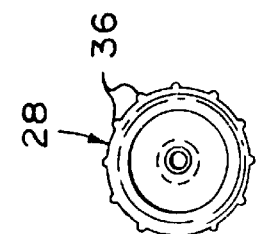
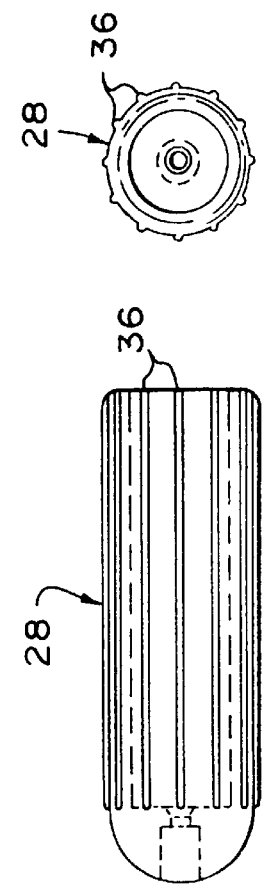
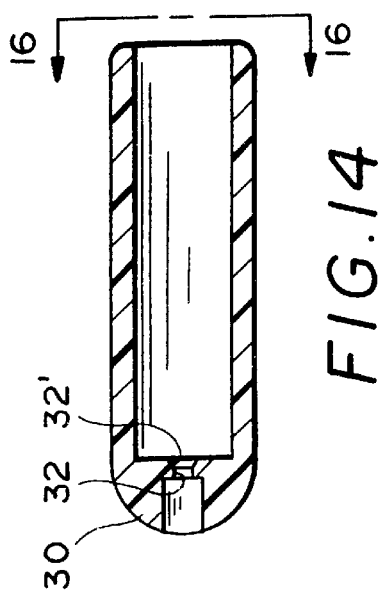

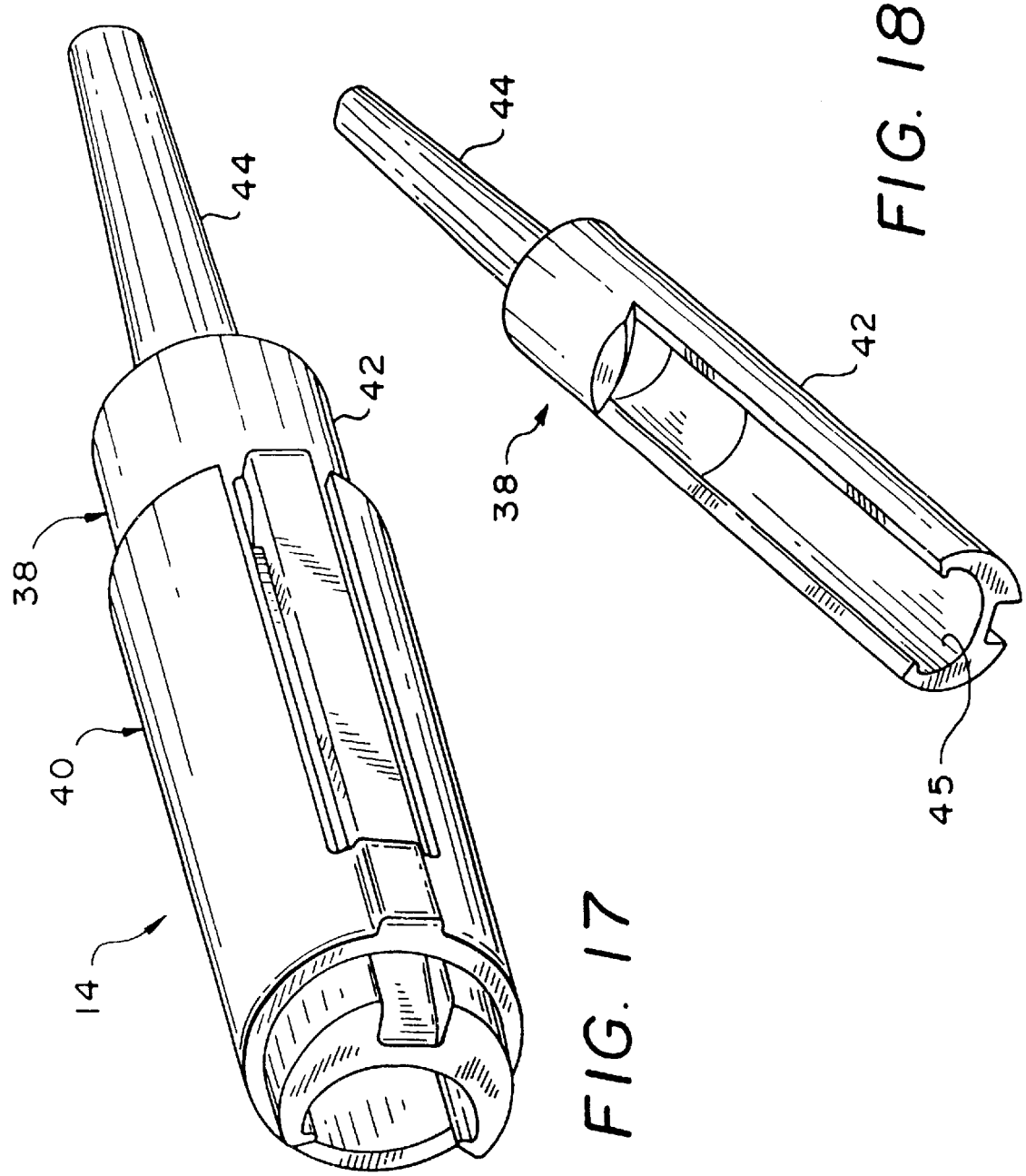

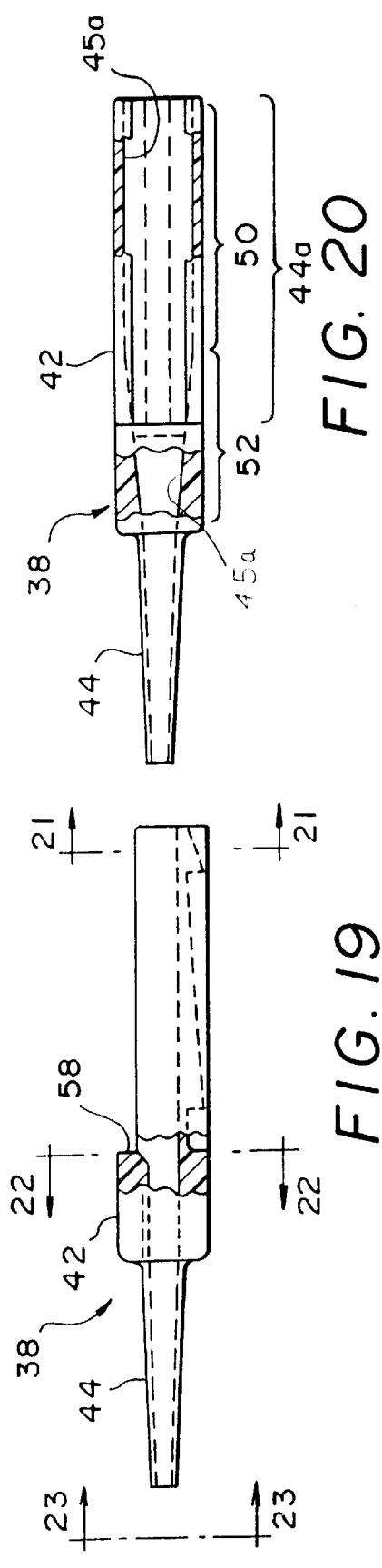
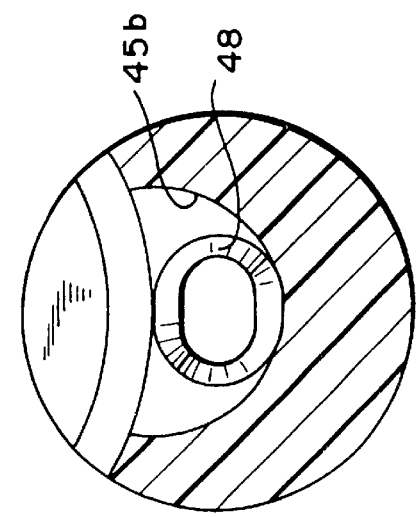
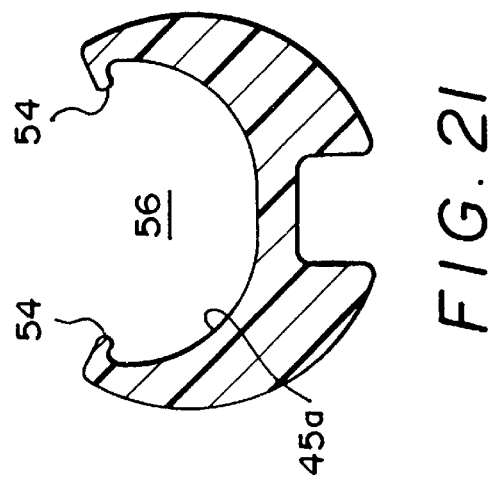

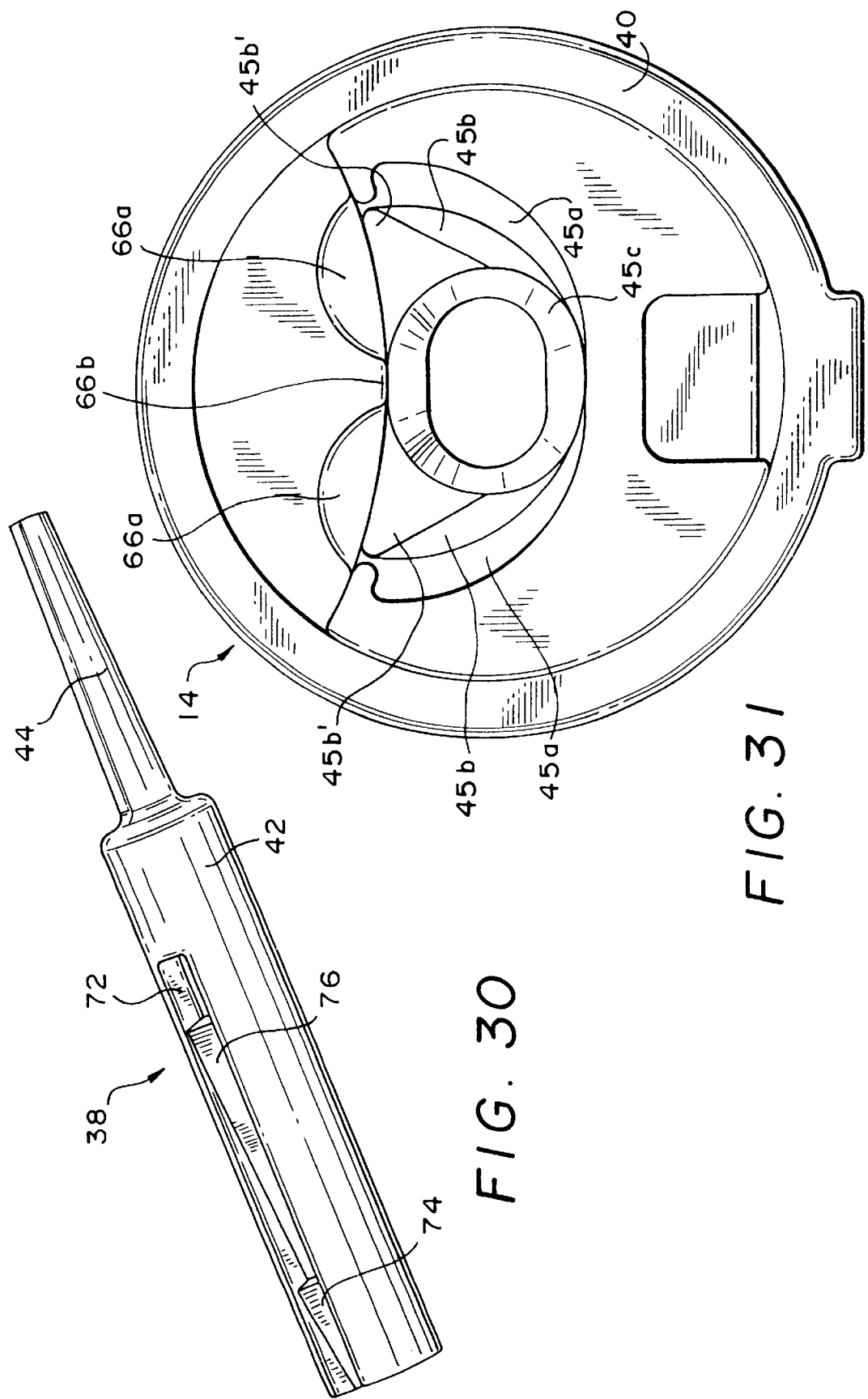

METHOD PRELOADING A DEFORMABLE INTRAOCULAR LENS INTO INJECTING APPARATUS FOR STORAGE AND/OR SHIPMENT

RELATED APPLICATION(S)

This application is a division of application No. 08/747,308, filed Nov. 12, 1996 (status: U.S. Pat. No. 5,728,102); which is a File Wrapper Continuation of Ser. No. 08/345,360, filed Nov. 18, 1994 (status: abandoned).

This is a continuation-in-part of U.S. patent application entitled "INTRAOCULAR LENS INSERTION SYSTEM", Ser. No. 07/953,251 filed on Sep. 30, 1992, now abandoned; U.S. patent application entitled "METHODS OF IMPLANTATION OF INTRAOCULAR LENS", Ser. No. 08/195,717 filed on Feb. 14, 1994, now abandoned; U.S. patent application entitled "HINGELESS INTRAOCULAR LENS MICROCARTRIDGES, Ser. No. 08/196,855 filed on Feb. 15, 1994, now U.S. Pat. No. 5,436,770; U.S. patent application entitled "INTRAOCULAR LENS MICROCARTRIDGE, Ser. No. 08/197,604 filed on Feb. 17, 1994, now U.S. PAt. No. 5,499,987, U.S. patent application entitled "METHOD FOR THE SURGICAL IMPLANTATION OF A DEFORMABLE INTRAOCULAR LENS IN THE EYE", Ser. No. 08/220,999 filed on Apr. 1, 1994, now abandoned, and U.S. patent application Ser. No. 08/225,060 entitled "INTRAOCULAR LENS INJECTION SYSTEM-"filed on May 10, 1994, now pending, and all fully incorporated by reference herein.

FIELD OF THE INVENTION

This invention relates to an intraocular lens insertion system having one or more disposable components, in particular an intraocular injection system comprising two separate main components including a disposable injecting device and a disposable cartridge.

BACKGROUND OF THE INVENTION

The intraocular lens injection system currently being sold and marketed by STAAR Surgical Company of California has gain widespread acceptance in the field of intraocular lens replacement. The current system utilizes an injector made of titanium so that the unit can be autoclaved and reused numerous times. The components of the titanium injector are machined from bar stock to a high degree of accuracy according to current specifications, and then the components are assembled into the final injector unit. The cost of the materials, and labor costs involve with machining and assembly are substantial providing an incentive to seek less expensive alternatives. Further, the steps of cleaning and autoclaving the injector unit between operations is a time burden and nuisance to busy surgeon practitioners having back-to-back operation schedules. In addition, the injector must be properly autoclaved to ensure complete cleaning and sterilization to prevent spread of diseases causing eye infections or other infectious diseases, prevent transmission of body fluid and prevent resulting liability problems to surgeon practitioners. These any other considerations have led to the development of the present invention.

SUMMARY OF THE INVENTION

An object of the present invention is to provide a disposable intraocular lens insertion system.

A second object of the present invention is to provide one or more disposable components of an intraocular lens insertion system.

A third object of the present invention is to provide a disposable intraocular lens insertion system comprising two main separate components including a disposable injecting device and disposable cartridge.

A fourth object of the present invention is to provide a disposable injecting device for an intraocular lens injection system.

A fifth object of the present invention is to provide a disposable cartridge for an intraocular lens injection system.

A sixth object of the present invention is to provide a disposable cartridge having a downwardly tapering passageway for further folding the intraocular lens as it moves through the cartridge.

A seventh object of the present invention is to provide a disposable cartridge unit including a disposable cartridge containing a preloaded foldable intraocular lens.

An eighth object of the present invention is to provide a two-piece disposable cartridge system comprising a lens holding portion and a sleeve portion.

A ninth object of the present invention is to provide an intraocular lens injecting system comprising a cartridge, which front loads and locks to a injecting device.

A tenth object of the present invention is to provide an intraocular lens injecting system having a pre-loaded intraocular lens for storage and shipment.

An eleventh object of the present invention is to provide an intraocular lens injecting system comprising an injecting device and cartridge with an intraocular lens pre-loaded in the cartridge for storage and shipment.

These and other objects can be achieved by various embodiments of the present invention. Specifically, one or more components of the intraocular lens insertion system according to the present invention are disposable. Preferably, the entire system excluding the intraocular lens itself is disposable to provide the full advantages according to the present invention.

The components of the intraocular lens insertion system according to the present invention must withstand sterilization methods, in particular autoclaving, in order to be practically utilized. Preferably, the components of the intraocular lens insertion system according to the present invention are made from plastic, most preferably autoclavable plastic (i.e. plastic having a melting point above approximately 121 degree Celsius) such as polysulfone, polycarbonate, nylon-66, TEFLON and KYNAR that can withstand the conditions of high temperature and pressure inside conventional autoclaving units. Further, the use of plastic allows the components of the intraocular injection system to be injection molded and quickly assembled significantly reducing cost in the construction thereof verses a stainless steel injector.

An embodiment of the disposable injection system comprises two separate main components including an injecting device having a barrel with a cartridge receiver for accommodating a cartridge, and a cartridge for accommodating a foldable intraocular lens. The injecting device preferably includes a cylindrical barrel having one end open, and an opposite end fitted with a movable plunger. Specifically, the end fitted with the movable plunger is provided with a guide for defining a passageway for accommodating the movable plunger. The guide is preferably molded as part of the inside of the cylindrical barrel, however, alternatively can be made as a separate piece and then assembled in some suitable manner inside the cylindrical barrel.

The guide preferably is configured to allow sliding movement of the movable plunger in a longitudinal direction with relation to the cylindrical barrel, however, not allowing rotational movement of the movable plunger with respect to the cylindrical barrel. For example, the guide is provided with a keyway preventing relative rotation. In one preferred embodiment, the passageway through the guide has a passageway with a cross-sectional shape matching a movable plunger preventing relative rotation.

The open end of the cylindrical barrel provides a cylindrical shaped receiver for accommodating the cartridge containing the intraocular lens. Further, the open end of the cylindrical barrel is provided with means for connecting and securely retaining the cartridge inside the front open end of the cylindrical barrel. For example, a snap fit connection is provided between the cylindrical barrel and cartridge so that when the cartridge is inserted in the end of the cylindrical barrel these components snap fit together forming a secure connection. Alternatively or in addition, an interference type connection can be provided between the open front end of the cylindrical barrel and the cartridge so that these components are securely connected together when inserting the cartridge into the open end of the cylindrical barrel. The interference connection can be provided by sizing the outer dimensions of the cartridge slightly greater than the inner dimension of the open end of the barrel. Further, one or both components can have tapering outer surfaces or taps that interfere with each other to provide the interference type connection.

One end of the plunger is provided with a manipulating tip for making contact with the intraocular lens, forcing the intraocular lens from the cartridge, and manipulating the intraocular lens inside the eye, and an opposite end provided with means for actuating the plunger. The opposite end can be provided with a freely rotating finger tip gripping device to allow a user to exert sufficient pressure on the end of the plunger to controllably force the intraocular lens from the cartridge. For example, the finger tip gripping device is provided with a fluted exterior surface to facilitate gripping thereof, and a through hole having a predetermined size. The end of the plunger component is provided with an extension having a hooked end that can be forced into and through the through hole in the finger tip gripping device providing a snap connection between these components, and also allowing free rotation between these components.

The manipulating end is faceted in a particular manner to prevent damage to the intraocular lens, particularly the trailing haptic, during the step of forcibly pushing the intraocular lens through the nozzle of the cartridge and into the eye.

The disposable cartridge can have a variety of configurations. A preferred embodiment according to the present invention involves a two-piece cartridge system. A lens holding portion of the disposable cartridge is defined by an outer cylindrical surface having a wall portion partially removed along the upper length of a body portion thereof defining a longitudinal access opening into the lens holder portion. The lower side of the body portion is provided with a groove and two ramp type catches provided to define a snap fit connection with a cantilever spring as part of the outer cylindrical sleeve portion to be described in detail below.

The lens holder portion is provided with an inner surface having a C-shaped cross-sectional shape. Further, at the end of the lens holder portion opposite to the nozzle portion, a groove is provided in the inner surface to accommodate a trailing haptic when the intraocular lens is loaded inside the cartridge. In addition, the inside surface of the lens holder portion is provided with a pair of longitudinal protrusions running along the inside edges of the longitudinal access opening in the lens holder portion serving to secure the edges of the loaded foldable intraocular lens to prevent inadvertent movement or dislodging of the intraocular lens from the cartridge and used as guides to slide the lens and fold it during the advancement of the plunger forward.

The lens holder portion includes a nozzle portion, having a oral-shaped cross-sectional inner wall, disposed at one end of the body portion forming a one-piece plastic molded construction. Importantly, the passageway through the body portion is continuous and transitions with the passageway through the nozzle portion. Specifically, the inner wall defining the passageway through the body portion is continuous and smoothly transitions with the inner wall defining the passageway through the nozzle portion. At the transition between the body portion and nozzle portion is a tapering transition portion having downwardly tapering wall surfaces, since the inner width dimension of the C-shaped cross-sectional passageway through the body portion is wider than the inner width dimension of the oval-shaped cross-sectional passageway through the nozzle portion.

An intraocular lens is loaded into the cartridge by resting the lens on top of the body portion so that it bridges the sides of the longitudinal opening in the open passageway of the body portion. Tweezers or some other suitable manipulating instrument is used to press against the center of the intraocular lens in a downward direction so that the intraocular lens bends in the center along the longitudinal opening with the sides of the opening acting as guides for supporting outer edges of the intraocular lens. The intraocular lens is forced downwardly until it is fully loaded into the body portion in a folded configuration, specifically, a C-shaped folded configuration matching the C-shaped cross-section inner walls of the body portion. In the embodiment of the cartridge having foldable portions, the intraocular lens can be loaded flat into the cartridge and folded into a C-shaped configuration as it is being loaded into the injecting device.

The two-piece cartridge system includes a sleeve portion, preferably a cylindrical or oval shaped sleeve portion, that surrounds the body portion of the lens holding portion. The cylindrical sleeve portion has an outer cylindrical surface to be received within the open end receiver of the cylindrical barrel of the injector. The cylindrical sleeve portion can be provided with a longitudinal protrusion or key to be received within a longitudinal groove or keyway inside the open end receiver of the cylindrical barrel of the injector. This arrangement prevents rotation of the lens holder portion within the cylindrical sleeve portion.

The wall of the cylindrical sleeve portion is provided with a pair of set apart slits extending in the longitudinal direction of the cylindrical sleeve portion defining a cantilever spring provided with a hooked end or catch that cooperates with the pair of ramp type catches provided in the groove in the lower side of the lens holder portion of the cartridge defining the snap fit connection therebetween. Specifically, the catch of the cantilever spring of the cylindrical sleeve portion cooperates with one catch in the groove in the lens holder portion to prevent the cylindrical sleeve portion to be removed from the lens holder portion. In this position, the cartridge is in a configuration for loading the intraocular lens into the cartridge. When the cartridge is closed after loading the intraocular lens into the lens holding portion, the catch of the cantilever spring of the cylindrical sleeve portion cooperates with the other catch in the groove in the lens holder portion to lock the cylindrical sleeve portion in the closed position on the lens holder portion.

The present invention includes the concept of pre-loading the intraocular lens in the injection system. Specifically, a potentially preferred method of making and selling intraocular lens is to pre-load the intraocular lens in the injection device for purposes of storage and shipping. For example, the intraocular lens can be manufactured, and then placed inside the injecting device or cartridge (i.e. inside injecting system) prior to being packaged and shipped to a customer. This method reduces the amount of packaging by not requiring separate packages for the intraocular lens and the cartridge and/or injecting device. Further, the cartridge and/or injecting device protects the intraocular lens during the process of packaging, shipping and other handling, and eliminates the step of loading the intraocular lens into the cartridge and/or injecting device that could potentially cause damage thereto.

This method would allow the cartridge and/or injecting device and pre-loaded intraocular lens to be autoclaved together prior to injection of the intraocular lens.

BRIEF DESCRIPTION OF THE DRAWINGS

FIG. 1 is a perspective view of a preferred embodiment of the intraocular lens injection system according to the present invention.

FIG. 2 is a side longitudinal cross-sectional view of the intraocular lens injection system shown in FIG. 1.

FIG. 3 is a longitudinal side cross-sectional view of the cylindrical barrel of the intraocular lens injection system shown in FIG. 2.

FIG. 4 is a transverse cross-sectional view through the movable plunger, guide, and cylindrical barrel, as indicated in FIG. 2, to illustrating the movable plunger guiding arrangement.

FIG. 5 is a longitudinal side elevational view of the plunger portion having the manipulating tip.

FIG. 6 is a transverse cross-sectional view of the plunger portion, as indicated in FIG. 5.

FIG. 7 is a transverse cross-sectional view of the plunger portion, as indicated in FIG. 5.

FIG. 8 is a transverse cross-sectional view of the plunger portion, as indicated in FIG. 5.

FIG. 9 is an end elevation view of the manipulating tip of the plunger portion shown in FIG. 5.

FIG. 10 is a longitudinal side elevational view of the plunger portion that connects to the plunger portion shown in FIG. 5.

FIG. 11 is an end elevational view of the plunger portion shown in FIG. 10.

FIG. 12 is a transverse cross-sectional view of the plunger portion, as indicated in FIG. 10.

FIG. 13 is a transverse cross-sectional view of the plunger portion, as indicated in FIG. 11.

FIG. 14 is a cross-sectional view of the gripping device to be connected to the plunger, as shown in FIG. 2.

FIG. 15 is a side elevational view of the gripping device shown in FIG. 14.

FIG. 16 is an end elevational view of the gripping device shown in FIG. 14.

FIG. 17 is a perspective view of a preferred cartridge according to the present invention.

FIG. 18 is a perspective view of the lens holding portion of the preferred cartridge shown in FIG. 17.

FIG. 19 is a is a longitudinal side elevational view of the lens holding portion shown in FIG. 18.

FIG. 20 is a top planar view of the lens holding portion shown in FIG. 18.

FIG. 21 is a transverse cross-sectional view of the of the lens holding portion, as indicated in FIG. 19.

FIG. 22 is a transverse cross-sectional view of the lens holding portion, as indicated in FIG. 19.

FIG. 23 is an end elevational view of the end of the lens holding portion as indicated in FIG. 19.

FIG. 30 is another perspective view of the lens holding portion showing the longitudinal groove in the wall of the lens holding portion with a pair of ramp catches.

FIG. 31 is an end elevational view of the preferred cartridge shown in FIG. 17 revealing the detailed configuration of the lens guiding surfaces inside the cartridge.

DETAILED DESCRIPTION OF PREFERRED EMBODIMENTS

Figure 25:
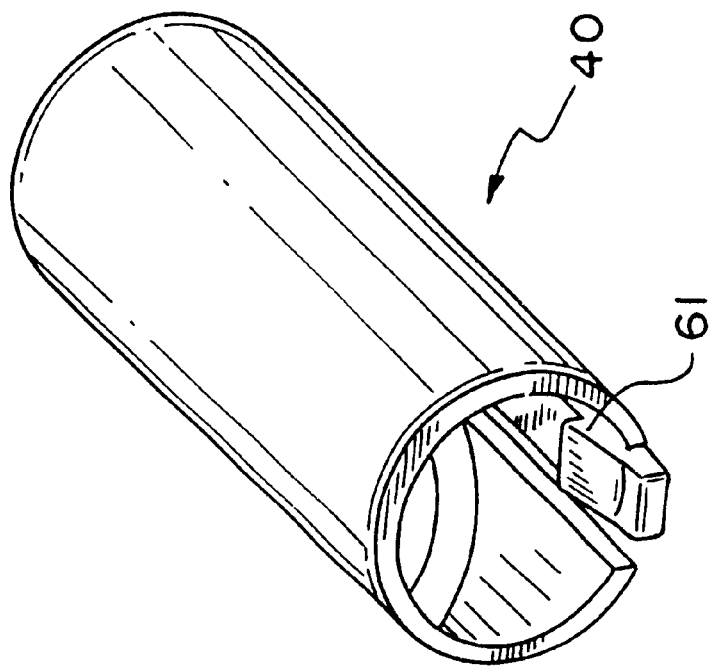
FIG. 25 is another perspective view of the sleeve portion of the preferred cartridge shown in FIG. 17.
Figure 24:
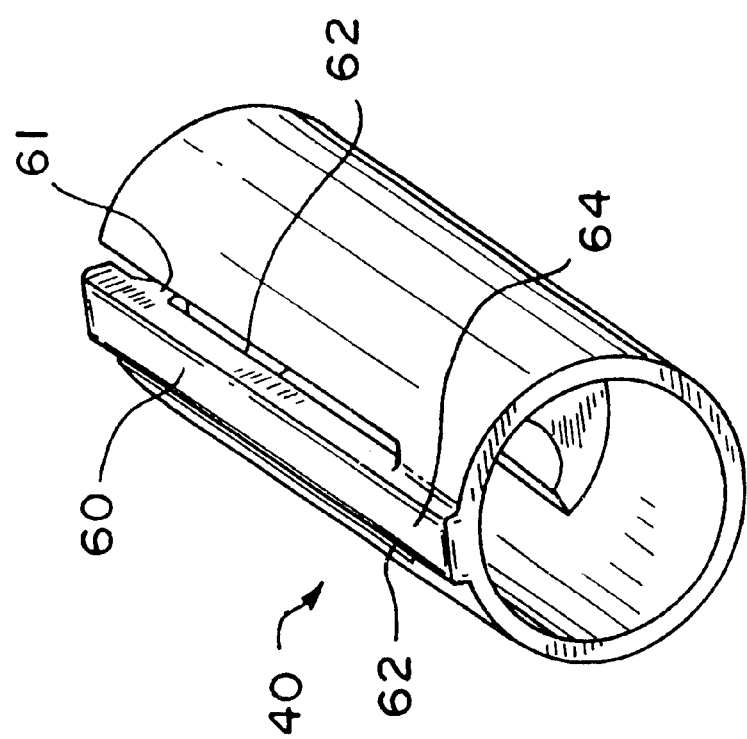
FIG. 24 is a perspective view of the sleeve portion of the preferred cartridge shown in FIG. 17.
Figure 27:
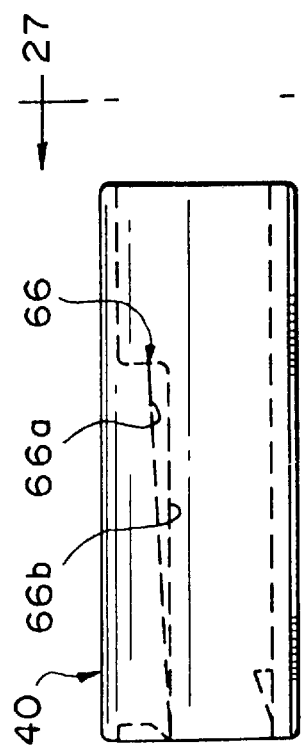
FIG. 27 is longitudinal side elevational view of the sleeve portion shown in FIG. 24 with ghost images of the guiding surfaces of the protrusion located inside the sleeve portion.
Figure 29:
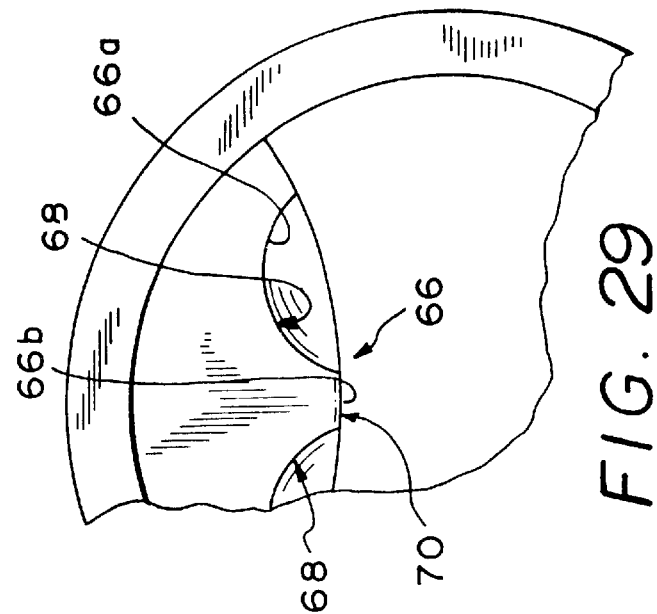
FIG. 29 is an exploded partial end elevational view of the sleeve portion shown in FIG. 27.
Figure 26:
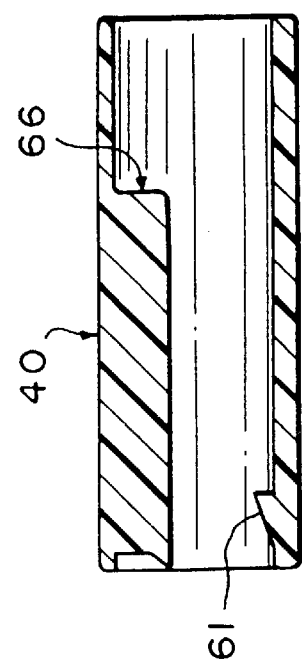
FIG. 26 is a longitudinal cross-sectional view of the sleeve portion shown in FIG. 24.

The term intraocular lens injection system according to the present invention is used to define two separate main components including an injecting device and a cartridge. The injecting device includes a cartridge receiver for accommodating a cartridge, and the cartridge is configured to accommodate a foldable intraocular lens. The foldable intraocular lens is first loaded into the cartridge, and then the cartridge is loaded into the injecting device providing an intraocular lens injection system readied for conducting the implantation operation.

The term disposable in the context of the present invention is to indicate that the one or more components of the intraocular lens injection system according to the present invention can be readily discarded after use due to the inexpensive nature of the design, construction, and materials of the components. The use of disposable components provides a variety of convenience factors such as preloading disposable cartridges with foldable intraocular lens, improved handling characteristics, reducing weight, and most importantly ensuring a high level of sterility protecting the patient from disease.

A preferred embodiment of the intraocular lens injection system 10 according to the present invention is shown in FIG. 1. The intraocular lens injection system comprises two main components including an injecting device 12 and a cartridge 14.

The injecting device 12 comprises a cylindrical barrel 16 having a cartridge receiver 18 located at one end thereof, as shown in FIG. 2. The barrel 16 can have other suitable cross-sectional shapes, however, a cylindrical-shaped barrel is particular suitable for making, assembling, and utilizing the injecting device 12. The cartridge receiver 18 accommodates the cartridge 14, which is securely connected to the injecting device 12 when inserted into the cartridge receiver 18. For example, an interference type connection can be provided between the injecting device 12 and cartridge 14 by making one or more outer dimensions of the cartridge 14 slightly larger than one or more inner dimensions of the cartridge receiver 18. Alternatively or in addition, a snap type connection can be provided between the injecting device 12 and cartridge 14. Further, either or both type of connections can be made so that the cartridge is either removable or non-removable after insertion into the cartridge receiver 18. Preferably, the injecting device 12 and cartridge 14 are designed so that the cartridge 14 can not be rotated within the cartridge receiver 18 to prevent any relative movement therebetween which can detract from the manipulating characteristics of the intraocular lens injection system.

The design of the cylindrical barrel 12 itself is shown in FIG. 3. The barrel comprises a portion 12a having thicker walls to provide structural strength against bending in the longitudinal direction, and a portion 12b having thinner walls defining the cartridge receiver 18. An inner edge 18a at the transition between the portions 12a and 12b defines a stop for the cartridge 14 when inserted into the cartridge receiver 18.

The injecting device 12 further includes a movable plunger 20 disposed within the cylindrical barrel 16. Specifically, the movable plunger 20 is movable disposed within the cylindrical barrel for movement forward or backwards with respect to the longitudinal direction of the cylindrical barrel 12. The movable plunger 20 includes a manipulating tip 22 for engaging with the intraocular lens for forcing the intraocular lens from the loaded cartridge 14. In the intraocular lens injection system 10, the plunger 20 comprises two plunger portions 20a and 20b, as shown in FIGS. 2, 5 and 6. The two portions 20a and 20b can have a one-piece construction, or can be made as two separate pieces connected together is some suitable manner.

The detailed design of the plunger portion 20a of the movable plunger 20 is shown in FIGS. 5 to 9, and the detailed design of the plunger portion 20b of the movable plunger 20 is shown in FIGS. 10 to 13.

The plunger portion 20a includes a connector portion 21a (FIG. 5) for connecting with a connector portion 21b (FIG. 10) of the plunger portion 20b. Preferably, an interference type connection and/or snap fit type connection is provided by the connector portions 21a and 21b to facilitate assembly. In the embodiment shown, a keyway type connection is provided by the flat surfaces 21a' of the connector portion 21a (FIG. 6) cooperating with the flat key surface 21b' of the connector portion 21b (FIG. 13). The keyway type connection prevents relative rotation between the plunger components 20a and 20b after the plunger 20 is assembled.

The detail design of the manipulating tip 22 is shown in FIG. 9. The manipulating tip 22 is defined by a plurality of facets for manipulating the intraocular lens from the cartridge and in the eye. Specifically, the manipulating tip comprises a curved surface facet 22a, curved surface facet 22b, concave surface facet 22c, upper protrusion facet 22d, and lower protrusion facet 22e.

In the preferred embodiment of the intraocular lens injection system 10, the movable plunger 20 is slidably disposed within the cylindrical barrel 12. Specifically, a guide 24 is disposed within the cylindrical barrel 12, which guide 24 is provided with a passageway 26 for slidably supporting the movable plunger 20. In the embodiment shown, the inner dimensions of the passageway 26 of the guide 24 are slightly greater than the outer dimensions of the movable plunger 20 to provide the guide arrangement. Further, the cross-section shape of the passageway 26 is preferably made the same as the cross-sectional shape of the movable plunger 20 (i.e. matching shapes) to enhance a close tolerance fit therebetween to improve sliding accuracy. More preferably, the cross-sectional shapes of the passageway 26 of the guide 24 and the movable plunger 20 are interlocking to prevent relative rotation between the cylindrical barrel 12 fixed to the guide 24 and the movable plunger 12, again to enhance the manipulating characteristics of the intraocular lens injection system 10. For example, the cross-sectional shapes of the passageway 26 of the guide 24 and the movable plunger 20 can be cross-shaped to provide an interlocking arrangement, as shown in FIG. 4.

In the embodiment shown in FIG. 2, the guide 24 is part of the cylindrical barrel 12. For example, the cylindrical barrel 12 can be injection molded from plastic to include the guide 24 as a one-piece unit. Alternatively, the guide 24 can be made as a separate piece, and then assembled inside the cylindrical barrel 12. Further, in the embodiment shown, the guide 24 is provided at one end of the cylindrical barrel 12, however, the guide 24 can be located at a position inside the cylindrical barrel 12 away from the end of the cylindrical barrel 12.

The movable plunger 20 is provided with a finger tip gripping device 28 located at an end opposite to the manipulating tip 22. The gripping device 28 is preferably connected in a freely rotating manner with the end of the plunger 20, however, a non-rotating type connection can also be utilized.

In the preferred embodiment of the intraocular injection system 10, the gripping device is essentially cylindrical-shaped, and having an inner diameter slightly greater than the outer diameter of the cylindrical barrel 12 to allow an end portion of the cylindrical barrel 12 to be accommodated inside the gripping device 28 when the movable plunger 20 is moved towards the right in FIG. 1. The outer surface of the gripping device can be fluted to increasing the gripping ability by a user's finger tips.

The gripping device 28 is provided with an end portion 30 having a passageway 32 for accommodating a protrusion 34 having a hooked end portion 35 of the movable plunger 20. Specifically, the hooked end portion 34 is provided with a conical tapering surface 35a having a lip 35b (FIG. 11) with a slightly greater diameter than the passageway 32 in the end portion 30 to provide a snap fit connection therebetween. Thus, the gripping device 28 can be easily assembled onto the movable plunger 20 by forcing the hooked end portion through the passageway 32.

The detailed design of the gripping device 28 is shown in FIGS. 14 to 16.

In FIG. 14, the passageway 32 in the end portion 32 of the gripping device 28 is provided with a conical tapering surface 32' to facilitate entry of the hooked end 35 of the plunger 20 into and through the passageway 32 during assembly. The outside of the gripping device 28 can be provided with a plurality of longitudinal ribs 36 equally spaced around the perimeter of the gripping device 28, as shown in FIGS. 15 and 16.

A preferred embodiment of the cartridge 14 is shown in FIGS. 17 to 28.

The cartridge 14 comprises two main separate components including a lens holding portion 38 and a sleeve portion 38. The lens holding portion 38 is defined by a body portion 42 having a passageway 45, and a nozzle portion 46 having a passageway 48, as shown in FIGS. 18 to 22.

The body portion 42 is defined by a lens receiving portion 50 and a lens transition portion 52, as shown in FIG. 20. The lens receiving portion 50 has a fixed cross-sectional size and shaped passageway 45a (FIGS. 20 and 21). Specifically, the lens receiving portion 50 has a C-shaped cross section defining the open passageway 44a that does not vary in shape or size along the length of the lens receiving portion 50. Further, the lens transition portion 52 has a variable or downwardly tapering cross-sectional size and shape closed passageway 45b (FIGS. 20 and 22). Specifically, the transition portion 52 initially has a C-shaped cross section defining the beginning of closed passageway 45b and matching passageway 45a, however, the shape changes from C-shaped (i.e. open passageway design), to D-shaped (i.e. closed passageway design), to oval (i.e. closed passageway design) along the length of the lens transition portion 52.

The lens receiving portion 50 and an initial portion of the lens transition portion having a C-shaped cross section passageway include a pair of gripping edge protrusions 54 positioned on either side of opening 56 into passageway 45a. The gripping edge protrusions 54 grip the outer edges of the folded intraocular lens once inserted into the lens receiving portion 50.

The nozzle portion 44 is located at one end of the body portion 42. Preferably, the lens holding portion 38 including the body portion 42 and nozzle portion 44 are a molded one-piece construction.

The nozzle portion 44 having passageway 48 has an oval-shaped cross-sectional shape. However, the cross-sectional size tapers downwardly from the body portion 42 to the end of the nozzle portion 44 (See tapering passageway 48 in FIG. 22).

The detailed design of the sleeve portion 40 is shown in FIGS. 24 to 29.

The sleeve portion 40 is essentially cylinder-shaped. Specifically, the inner diameter is approximately equal to the outer diameter of the cylindrical body portion 42 of the lens holding portion 38. The cartridge 14 is assembled by inserting the body portion 42 of the lens holding portion into the sleeve portion 40 until the end of the sleeve portion contacts with the edge 58 (FIG. 19) of the lens holding portion 38.

The sleeve portion 40 includes a cantilever spring 60 having a catch 61 provided at the end thereof. The cantilever spring 60 is formed by providing a pair of parallel slits 62 in the wall of the sleeve portion 40. Further, the cantilever spring 60 is thicker than the wall of the sleeve portion 40 and extends along a portion of the outside thereof defining a protrusion 64 forming a keyway with the cartridge receiver 18 of the cylindrical barrel 12 of the injecting device.

The sleeve portion 40 is provided with a lens guiding protrusion 66 extending from the inner surface thereof into an upper portion of the passageway 44 in the body portion 42. The lens guiding protrusion 66 is defined by a pair of downwardly tapering grooves 68, 68 (FIGS. 28 and 29) positioned side-by-side defining a center protrusion 70. Both the downwardly tapering grooves 68 having tapering lens guiding surfaces 66a and center protrusion 70 having tapering lens guiding surface 66b taper in such a manner as to close down the cross-sectional size of the open passageway 45a through the body portion 38.

Figure 28:
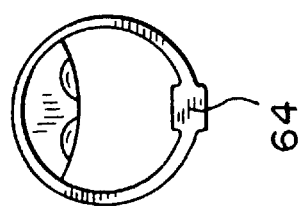
FIG. 28 is an end elevational view of the of the sleeve portion, as indicated in FIG. 27.

An outer portion of the lens holding portion 38 is provided with a longitudinal groove 72 having a pair of engaging ramp type catches 74 and 76 located in the groove 72, as shown in FIG. 28. The ramp type catches 74 and 76 cooperated with the catch 61 of the cantilever spring 60 to lock the sleeve portion 40 onto the lens holding portion at two different locations.

The detailed configuration of the lens guiding surfaces inside the cartridge 14 is shown in FIG. 31.

Figure 32:
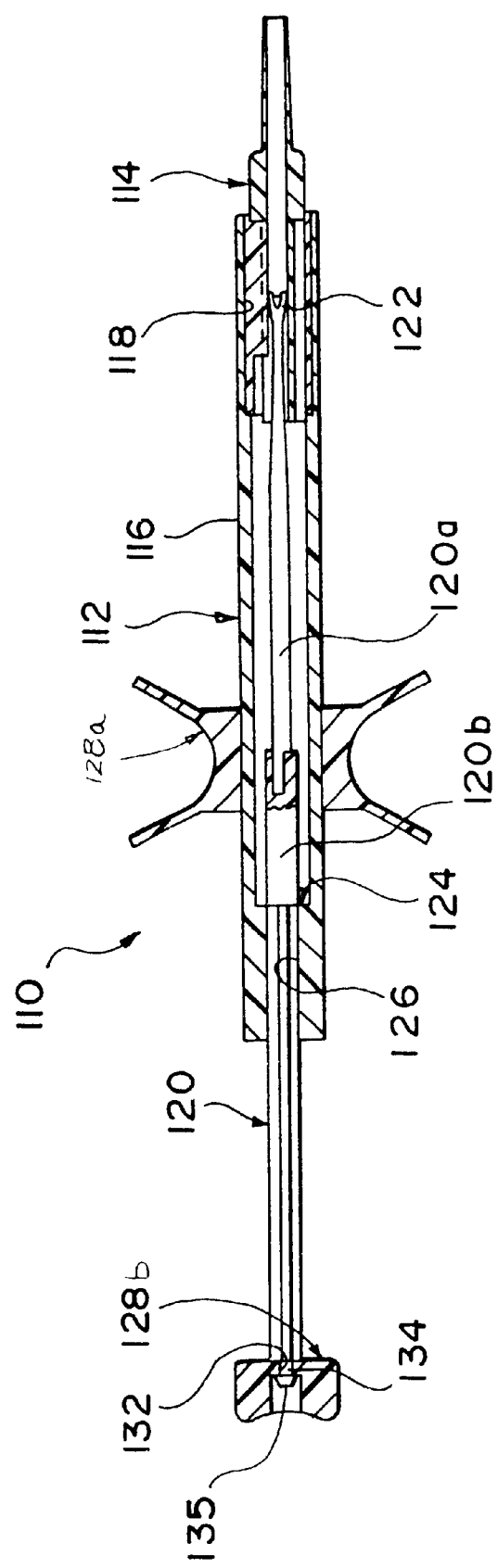
FIG. 32 is a longitudinal cross-sectional view of another embodiment of an injecting device according to the present invention.

Another embodiment of the injecting device 110 is shown in FIG. 32. This embodiment is provided with an a fingertip gripping device and a thumb gripping device 128, as shown to enhance manipulating and using the device.

The present invention includes the concept of pre-loading the intraocular lens in the injection system. Specifically, a potentially preferred method of making and selling intraocular lens is to pre-load the intraocular lens in the injection device for purposes of storage and shipping. For example, the intraocular lens can be manufactured, and then placed inside the injecting device or cartridge (i.e. inside injecting system) prior to being packaged and shipped to a customer. This method reduces the amount of packaging by not requiring separate packages for the intraocular lens and the cartridge and/or injecting device. Further, the cartridge and/or injecting device protects the intraocular lens during the process of packaging, shipping and other handling, and eliminates the step of loading the intraocular lens into the cartridge and/or injecting device that could potentially cause damage thereto.

This method would allow the cartridge and/or injecting device and pre-loaded intraocular lens to be autoclaved together prior to injection of the intraocular lens.

We claim:

1. A method of implanting an intraocular lens with an intraocular lens injecting system, comprising the steps of:
   pre-loading an intraocular lens into an intraocular lens injecting system; and
   then packaging said intraocular lens injecting system with said pre-loaded intraocular lens.

2. A method according to claim 1, including the step of shipping the preloaded deformable intraocular lens.

3. A method according to claim 1, including the step of autoclaving the preloaded deformable intraocular lens.

4. A method according to claim 1, wherein the deformable intraocular lens is preloaded into a lens cartridge.

5. A method according to claim 4, wherein the lens cartridge includes an open delivery passageway portion leading into a closed lens delivery passageway portion, and the deformable intraocular lens is preloaded into the open delivery passageway portion of the lens cartridge.

6. A method according to claim 1, including the step of injecting the preloaded deformable intraocular lens in the lens injecting apparatus through the small incision in the eye for implanting the deformable intraocular lens.

7. A deformable lens injecting apparatus, comprising:
   a lens injecting apparatus including a preloaded deformable intraocular lens configured for storing the deformable intraocular lens.

8. An apparatus according to claim 7, wherein said lens injecting apparatus includes a lens delivery passageway, and said deformable intraocular lens is preloaded into the lens delivery passageway.

9. An apparatus according to claim 8, wherein said lens delivery passageway inwardly tapers downwardly in a direction of insertion of the deformable intraocular lens.

10. An apparatus according to claim 7, wherein said lens injecting apparatus includes a lens cartridge preloaded with the deformable intraocular lens.

11. An apparatus according to claim 10, including a lens injecting device provided with a lens cartridge receiver.

12. An apparatus according to claim 11, wherein said lens cartridge and lens cartridge receiver of said lens injecting device are configured so that the lens cartridge can be removable connected to said lens cartridge receiver of said lens injecting device.

13. A method of preloading a deformable intraocular lens into a lens injecting apparatus, and implanting an intraocular lens into an eye, said method comprising the steps of:

preloading a deformable intraocular lens into a lens cartridge of the lens injecting apparatus for storing the intraocular lens; and then packaging said lens cartridge containing said preloaded intraocular lens.

14. A method of using a deformable intraocular lens injecting apparatus for implanting an intraocular lens into an eye, said method comprising the steps of:

preloading a deformable intraocular lens into a portion of the lens injecting apparatus for storing the deformable intraocular lens for later use; and then packaging the portion of the deformable intraocular lens injecting apparatus containing the preloaded deformable intraocular lens.

15. A method of implanting a deformable intraocular lens into an eye using a deformable lens injecting apparatus, said method comprising the steps of:

preloading a deformable intraocular lens into a lens cartridge of the deformable intraocular lens injecting apparatus;

then packaging said lens cartridge containing said preloaded deformable intraocular lens;

then unpackaging said lens cartridge, and loading the lens cartridge into the deformable intraocular lens injecting apparatus; and inserting the deformable lens from the deformable intraocular lens injecting apparatus into the eye.

* * * * *